United States Patent [19]

Maroteaux

[11] Patent Number: 5,780,245
[45] Date of Patent: Jul. 14, 1998

[54] POLYPEPTIDES HAVING A SEROTONIN RECEPTOR ACTIVITY, NUCLEIC ACIDS CODING FOR THESE POLYPEPTIDES AND USES

[75] Inventor: Luc Maroteaux, Strasbourg, France

[73] Assignee: Institut National de la Sante et de la Recherche Medicale, Paris, France

[21] Appl. No.: 416,788

[22] PCT Filed: Oct. 13, 1993

[86] PCT No.: PCT/FR93/01012

§ 371 Date: Apr. 14, 1995

§ 102(e) Date: Apr. 14, 1995

[87] PCT Pub. No.: WO94/09130

PCT Pub. Date: Apr. 28, 1994

[30] Foreign Application Priority Data

Oct. 14, 1992 [FR] France .................................. 92 12280

[51] Int. Cl.$^6$ .................................................. C12N 15/00
[52] U.S. Cl. .......................... 435/7.21; 530/350; 536/23.5; 435/325; 435/252.3; 435/320.1
[58] Field of Search .................. 435/6, 7.2, 7.21, 435/320.1, 69.1, 172.3, 240.2, 252.34, 325; 536/23.5, 24.3, 24.31, 24.33; 530/350

[56] References Cited

FOREIGN PATENT DOCUMENTS

WO 89/08149  9/1989  WIPO .

OTHER PUBLICATIONS

EMBO J. 11(9):3481–87, 1992, Foguet Hoyer Pardo Parekh Kluxen et al., Cloning and functional characterization of the rat stomach fundus serotonin.

Dec. 31, 1991 Biochem. Biophys. Res. Commun. 181(3):1469–78, Saltzman Morse Whitman Ivanshchenko Jaye Felder, Cloning of the Human Serotonin 5–HT2 and 5–HT1C Receptor Subtypes.

FEBS Lett. 312(2,3): 203–07, Nov. 1992, Loric Launay Colas Maroteaux, New mouse 5–HT2–like receptor Expression in brain, heart and intestine.

Trends in Pharmacol. Sci. 10:64–69, 1989, Hartig, Molecular biology of 5–HT receptors.

Neuro Report 3:345–348, 1992, Foguet Nguyen Le Lubbert, Structure of the mouse 5–HT 1C, 5–HT2 and stomach fundus serotonin receptor genes.

Pharmacol. Rev. 44:401–458, 1992, Zifa Fillion, 5–Hydroxytryptamine Receptors.

Mol. Pharmacol. 42:549–57, 1992, Kursar Nelson Wainscott Cohen Baez, Molecular Cloning, Functional Expression, and Pharmacological Characterization of a Novel Serotonin Receptor (5–Hydroxytryptamine$_{2F}$) from Rat Stomach Fundus.

Pharm. Rev. 46(2):157–203, 1994, Hoyer Clarke Fozard Hartig Martin et al., International Union of Pharmacology Classification of Receptors for 5–Hydroxytryptamine (Serotonin).

Primary Examiner—Marianne P. Allen
Attorney, Agent, or Firm—Seidel, Gonda, Lavorgna & Monaco, PC

[57] ABSTRACT

The present invention concerns novel polypeptides designated 5HT2C having serotoninergic receptor activity, the genetic material permitting their expression, recombinant cells expressing these polypeptides and their use.

11 Claims, 2 Drawing Sheets

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
      ( A ) LENGTH: 1532 base pairs
      ( B ) TYPE: nucleic acid
      ( C ) STRANDEDNESS: double
      ( D ) TOPOLOGY: linear    ( i i ) MOLECULE TYPE: cDNA    ( i i i ) HYPOTHETICAL: NO    ( i v ) ANTI-SENSE: NO    ( i x ) FEATURE:
      ( A ) NAME/KEY: CDS (B) LOCATION: 19..1458

(xi) SEQUENCE DESCRIPTION: SEQ ID NO:1:

```
TGAGTCACCA AAAGGCGA ATG GCT TCA TCT TAT AAA ATG TCT GAA CAA AGC    51
                    Met Ala Ser Ser Tyr Lys Met Ser Glu Gln Ser
                     1               5                  10

ACA ACT TCT GAG CAC ATT TTA CAG AAG ACA TGT GAT CAC CTG ATC CTG    99
Thr Thr Ser Glu His Ile Leu Gln Lys Thr Cys Asp His Leu Ile Leu
             15                  20                  25

ACT AAC CGT TCT GGA TTA GAG ACA GAC TCA GTA GCA GAG GAA ATG AAG   147
Thr Asn Arg Ser Gly Leu Glu Thr Asp Ser Val Ala Glu Glu Met Lys
         30                  35                  40

CAG ACT GTG GAG GGA CAG GGG CAT ACA GTG CAC TGG GCA GCT CTC CTG   195
Gln Thr Val Glu Gly Gln Gly His Thr Val His Trp Ala Ala Leu Leu
     45                  50                  55

ATA CTC GCG GTG ATA ATA CCC ACC ATT GGT GGG AAC ATC CTT GTG ATT   243
Ile Leu Ala Val Ile Ile Pro Thr Ile Gly Gly Asn Ile Leu Val Ile
 60                  65                  70                  75

CTG GCT GTT GCA CTG GAG AAA AGG CTG CAG TAC GCT ACC AAC TAC TTT   291
Leu Ala Val Ala Leu Glu Lys Arg Leu Gln Tyr Ala Thr Asn Tyr Phe
                 80                  85                  90

TTA ATG TCC TTG GCG ATA GCA GAT TTG CTG GTT GGA TTG TTT GTG ATG   339
Leu Met Ser Leu Ala Ile Ala Asp Leu Leu Val Gly Leu Phe Val Met
             95                 100                 105

CCG ATT GCC CTC TTG ACA ATC ATG TTT GAG GCT ATA TGG CCC CTC CCA   387
Pro Ile Ala Leu Leu Thr Ile Met Phe Glu Ala Ile Trp Pro Leu Pro
        110                 115                 120

CTG GCC CTG TGT CCT GCC TGG TTA TTC CTC GAT GTT CTC TTT TCA ACT   435
Leu Ala Leu Cys Pro Ala Trp Leu Phe Leu Asp Val Leu Phe Ser Thr
    125                 130                 135

GCC TCC ATC ATG CAT CTC TGT GCC ATT TCC CTG GAC CGC TAT ATA GCC   483
Ala Ser Ile Met His Leu Cys Ala Ile Ser Leu Asp Arg Tyr Ile Ala
140                 145                 150                 155

ATC AAA AAG CCA ATT CAG GCC AAT CAG TGC AAC ACC CGG GCT ACT GCA   531
Ile Lys Lys Pro Ile Gln Ala Asn Gln Cys Asn Thr Arg Ala Thr Ala
                160                 165                 170

TTC ATC AAG ATT ACA GTG GTA TGG TTA ATT TCA ATA GGC ATC GCC ATC   579
Phe Ile Lys Ile Thr Val Val Trp Leu Ile Ser Ile Gly Ile Ala Ile
            175                 180                 185

CCA GTC CCT ATT AAA GGA ATC GAG ACT GAT GTG ATT AAT CCA CAC AAT   627
Pro Val Pro Ile Lys Gly Ile Glu Thr Asp Val Ile Asn Pro His Asn
        190                 195                 200

GTC ACC TGT GAG CTG ACA AAG GAC CGC TTT GGC AGT TTT ATG GTC TTT   675
Val Thr Cys Glu Leu Thr Lys Asp Arg Phe Gly Ser Phe Met Val Phe
    205                 210                 215

GGG TCA CTG GCT GCT TTC TTC GTA CCT CTC ACC ATC ATG GTA GTC ACT   723
Gly Ser Leu Ala Ala Phe Phe Val Pro Leu Thr Ile Met Val Val Thr
220                 225                 230                 235

TAC TTT CTC ACC ATT CAC ACT TTA CAG AAG AAA GCT TAC TTG GTC AAA   771
Tyr Phe Leu Thr Ile His Thr Leu Gln Lys Lys Ala Tyr Leu Val Lys
                240                 245                 250

AAT AAG CCA CCT CAA CGC CTA ACA CGG TGG ACT GTG CCC ACA GTT TTC   819
Asn Lys Pro Pro Gln Arg Leu Thr Arg Trp Thr Val Pro Thr Val Phe
            255                 260                 265

CTA AGG GAA GAC TCA TCC TTT TCA TCA CCA GAA AAG GTG GCA ATG CTG   867
Leu Arg Glu Asp Ser Ser Phe Ser Ser Pro Glu Lys Val Ala Met Leu
        270                 275                 280

GAT GGG TCT CAC AGG GAT AAA ATT CTA CCT AAC TCA AGT GAT GAG ACA   915
Asp Gly Ser His Arg Asp Lys Ile Leu Pro Asn Ser Ser Asp Glu Thr
    285                 290                 295
```

| | | | | | | | | | | | | | | | | |
|---|---|---|---|---|---|---|---|---|---|---|---|---|---|---|---|---|
| CTT | ATG | CGA | AGA | ATG | TCC | TCA | GTT | GGA | AAA | AGA | TCA | GCC | CAA | ACC | ATT | 963 |
| Leu | Met | Arg | Arg | Met | Ser | Ser | Val | Gly | Lys | Arg | Ser | Ala | Gln | Thr | Ile | |
| 300 | | | | 305 | | | | | 310 | | | | | | 315 | |
| TCT | AAT | GAG | CAG | AGA | GCC | TCG | AAG | GCC | CTT | GGA | GTC | GTG | TTT | TTC | CTT | 1011 |
| Ser | Asn | Glu | Gln | Arg | Ala | Ser | Lys | Ala | Leu | Gly | Val | Val | Phe | Phe | Leu | |
| | | | | 320 | | | | | 325 | | | | | 330 | | |
| TTT | CTG | CTT | ATG | TGG | TGC | CCC | TTT | TTT | ATT | ACA | AAT | CTA | ACT | TTA | GCT | 1059 |
| Phe | Leu | Leu | Met | Trp | Cys | Pro | Phe | Phe | Ile | Thr | Asn | Leu | Thr | Leu | Ala | |
| | | | 335 | | | | | 340 | | | | | 345 | | | |
| CTG | TGT | GAT | TCC | TGC | AAT | CAG | ACC | ACT | CTC | AAA | ACA | CTC | CTG | GAG | ATA | 1107 |
| Leu | Cys | Asp | Ser | Cys | Asn | Gln | Thr | Thr | Leu | Lys | Thr | Leu | Leu | Glu | Ile | |
| | | 350 | | | | 355 | | | | | 360 | | | | | |
| TTT | GTG | TGG | ATA | GGC | TAC | GTT | TCC | TCG | GGG | GTG | AAT | CCT | CTG | ATC | TAT | 1155 |
| Phe | Val | Trp | Ile | Gly | Tyr | Val | Ser | Ser | Gly | Val | Asn | Pro | Leu | Ile | Tyr | |
| 365 | | | | | 370 | | | | | 375 | | | | | | |
| ACA | CTC | TTC | AAT | AAG | ACA | TTT | CGG | GAA | GCA | TTT | GGC | AGG | TAC | ATC | ACC | 1203 |
| Thr | Leu | Phe | Asn | Lys | Thr | Phe | Arg | Glu | Ala | Phe | Gly | Arg | Tyr | Ile | Thr | |
| 380 | | | | | 385 | | | | | 390 | | | | | 395 | |
| TGC | AAT | TAC | CGA | GCC | ACA | AAG | TCA | GTA | AAA | GCA | CTT | AGG | AAG | TTT | TCC | 1251 |
| Cys | Asn | Tyr | Arg | Ala | Thr | Lys | Ser | Val | Lys | Ala | Leu | Arg | Lys | Phe | Ser | |
| | | | | 400 | | | | | 405 | | | | | 410 | | |
| AGT | ACA | CTT | TGT | TTT | GGG | AAT | TCA | ATG | GTA | GAA | AAC | TCT | AAA | TTT | TTC | 1299 |
| Ser | Thr | Leu | Cys | Phe | Gly | Asn | Ser | Met | Val | Glu | Asn | Ser | Lys | Phe | Phe | |
| | | | 415 | | | | | 420 | | | | | 425 | | | |
| ACA | AAA | CAT | GGA | ATT | CGA | AAT | GGG | ATC | AAC | CCT | GCC | ATG | TAC | CAG | AGC | 1347 |
| Thr | Lys | His | Gly | Ile | Arg | Asn | Gly | Ile | Asn | Pro | Ala | Met | Tyr | Gln | Ser | |
| | | 430 | | | | 435 | | | | | 440 | | | | | |
| CCA | ATG | AGG | CTC | CGA | TGT | TCA | ACC | ATT | CAG | TCC | TCA | TCA | ATC | ATC | CTC | 1395 |
| Pro | Met | Arg | Leu | Arg | Cys | Ser | Thr | Ile | Gln | Ser | Ser | Ser | Ile | Ile | Leu | |
| | 445 | | | | 450 | | | | | 455 | | | | | | |
| CTC | GAT | ACC | CTT | CTC | ACT | GAA | AAC | GAT | GGC | GAC | AAA | GCG | GAA | GAG | CAG | 1443 |
| Leu | Asp | Thr | Leu | Leu | Thr | Glu | Asn | Asp | Gly | Asp | Lys | Ala | Glu | Glu | Gln | |
| 460 | | | | | 465 | | | | | 470 | | | | | 475 | |
| GTC | AGC | TAC | ATA | TAG | CAGGAACGGG | | CCGGCCTCAT | | CTTGAGAGAG | | GGTGATGAGC | | | | | 1498 |
| Val | Ser | Tyr | Ile | * | | | | | | | | | | | | |
| | | | | 480 | | | | | | | | | | | | |

AGGACGCACG CGCACCATGG CAGGTTCAAG AGTG　　　　　　　　　　　　　　　　1532

( 2 ) INFORMATION FOR SEQ ID NO:2:

( i ) SEQUENCE CHARACTERISTICS:
　　　　　　　　( A ) LENGTH: 479 amino acids
　　　　　　　　( B ) TYPE: amino acid
　　　　　　　　( D ) TOPOLOGY: linear ( i i ) MOLECULE TYPE: protein ( x i ) SEQUENCE DESCRIPTION: SEQ ID NO:2:

| Met | Ala | Ser | Ser | Tyr | Lys | Met | Ser | Glu | Gln | Ser | Thr | Thr | Ser | Glu | His |
|---|---|---|---|---|---|---|---|---|---|---|---|---|---|---|---|
| 1 | | | | 5 | | | | | 10 | | | | | 15 | |
| Ile | Leu | Gln | Lys | Thr | Cys | Asp | His | Leu | Ile | Leu | Thr | Asn | Arg | Ser | Gly |
| | | | 20 | | | | | 25 | | | | | 30 | | |
| Leu | Glu | Thr | Asp | Ser | Val | Ala | Glu | Glu | Met | Lys | Gln | Thr | Val | Glu | Gly |
| | | | 35 | | | | | 40 | | | | | 45 | | |
| Gln | Gly | His | Thr | Val | His | Trp | Ala | Ala | Leu | Leu | Ile | Leu | Ala | Val | Ile |
| | 50 | | | | | 55 | | | | | 60 | | | | |
| Ile | Pro | Thr | Ile | Gly | Gly | Asn | Ile | Leu | Val | Ile | Leu | Ala | Val | Ala | Leu |
| 65 | | | | | 70 | | | | | 75 | | | | | 80 |
| Glu | Lys | Arg | Leu | Gln | Tyr | Ala | Thr | Asn | Tyr | Phe | Leu | Met | Ser | Leu | Ala |
| | | | | 85 | | | | | 90 | | | | | 95 | |

-continued

| | | | | | | | | | | | | | |
|---|---|---|---|---|---|---|---|---|---|---|---|---|---|
| Ile | Ala | Asp | Leu 100 | Leu | Val | Gly | Leu 105 | Val | Met | Pro | Ile 110 | Ala | Leu | Leu |
| Thr | Ile | Met 115 | Phe | Glu | Ala | Ile | Trp 120 | Pro | Leu | Pro | Leu 125 | Ala | Leu | Cys | Pro |
| Ala | Trp 130 | Leu | Phe | Leu | Asp | Val 135 | Leu | Phe | Ser | Thr | Ala 140 | Ser | Ile | Met | His |
| Leu 145 | Cys | Ala | Ile | Ser | Leu 150 | Asp | Arg | Tyr | Ile | Ala 155 | Ile | Lys | Lys | Pro | Ile 160 |
| Gln | Ala | Asn | Gln | Cys 165 | Asn | Thr | Arg | Ala | Thr 170 | Ala | Phe | Ile | Lys | Ile 175 | Thr |
| Val | Val | Trp | Leu 180 | Ile | Ser | Ile | Gly | Ile 185 | Ala | Ile | Pro | Val | Pro 190 | Ile | Lys |
| Gly | Ile | Glu 195 | Thr | Asp | Val | Ile | Asn 200 | Pro | His | Asn | Val | Thr 205 | Cys | Glu | Leu |
| Thr | Lys 210 | Asp | Arg | Phe | Gly | Ser 215 | Phe | Met | Val | Phe | Gly 220 | Ser | Leu | Ala | Ala |
| Phe 225 | Phe | Val | Pro | Leu | Thr 230 | Ile | Met | Val | Val | Thr 235 | Tyr | Phe | Leu | Thr | Ile 240 |
| His | Thr | Leu | Gln | Lys 245 | Lys | Ala | Tyr | Leu | Val 250 | Lys | Asn | Lys | Pro | Pro 255 | Gln |
| Arg | Leu | Thr | Arg 260 | Trp | Thr | Val | Pro | Thr 265 | Val | Phe | Leu | Arg | Glu 270 | Asp | Ser |
| Ser | Phe | Ser 275 | Ser | Pro | Glu | Lys | Val 280 | Ala | Met | Leu | Asp | Gly 285 | Ser | His | Arg |
| Asp | Lys 290 | Ile | Leu | Pro | Asn | Ser 295 | Ser | Asp | Glu | Thr | Leu 300 | Met | Arg | Arg | Met |
| Ser 305 | Ser | Val | Gly | Lys | Arg 310 | Ser | Ala | Gln | Thr | Ile 315 | Ser | Asn | Glu | Gln | Arg 320 |
| Ala | Ser | Lys | Ala | Leu 325 | Gly | Val | Val | Phe | Phe 330 | Leu | Phe | Leu | Leu | Met 335 | Trp |
| Cys | Pro | Phe | Phe 340 | Ile | Thr | Asn | Leu | Thr 345 | Leu | Ala | Leu | Cys | Asp 350 | Ser | Cys |
| Asn | Gln | Thr | Thr 355 | Leu | Lys | Thr | Leu | Leu 360 | Glu | Ile | Phe | Val | Trp 365 | Ile | Gly |
| Tyr | Val 370 | Ser | Ser | Gly | Val | Asn 375 | Pro | Leu | Ile | Tyr | Thr 380 | Leu | Phe | Asn | Lys |
| Thr 385 | Phe | Arg | Glu | Ala | Phe 390 | Gly | Arg | Tyr | Ile | Thr 395 | Cys | Asn | Tyr | Arg | Ala 400 |
| Thr | Lys | Ser | Val | Lys 405 | Ala | Leu | Arg | Lys | Phe 410 | Ser | Ser | Thr | Leu | Cys 415 | Phe |
| Gly | Asn | Ser | Met 420 | Val | Glu | Asn | Ser | Lys 425 | Phe | Phe | Thr | Lys | His 430 | Gly | Ile |
| Arg | Asn | Gly 435 | Ile | Asn | Pro | Ala | Met 440 | Tyr | Gln | Ser | Pro | Met 445 | Arg | Leu | Arg |
| Cys | Ser 450 | Thr | Ile | Gln | Ser | Ser 455 | Ser | Ile | Ile | Leu | Leu 460 | Asp | Thr | Leu | Leu |
| Thr 465 | Glu | Asn | Asp | Gly | Asp 470 | Lys | Ala | Glu | Glu | Gln 475 | Val | Ser | Tyr | Ile 480 |

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear (  i  i  ) MOLECULE TYPE: peptide (  i  i  i ) HYPOTHETICAL: NO (  v  ) FRAGMENT TYPE: internal (  x  i ) SEQUENCE DESCRIPTION: SEQ ID NO:3:

| Ala | Ser | Pro | Ser | Gln | Ser | Leu | Leu | Lys | Glu | Ser | Arg | Leu | Met |
|-----|-----|-----|-----|-----|-----|-----|-----|-----|-----|-----|-----|-----|-----|
| 1   |     |     |     | 5   |     |     |     |     | 10  |     |     |     |     |

( 2 ) INFORMATION FOR SEQ ID NO:4:

(  i  ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear     (  i  i  ) MOLECULE TYPE: other nucleic acid     (  i  i  i ) HYPOTHETICAL: NO     (  i  v ) ANTI-SENSE: NO     (  i  x ) FEATURE:
        ( A ) NAME/KEY: modified_base
        ( B ) LOCATION: 19
        ( D ) OTHER INFORMATION: /mod_base=i     (  i  x ) FEATURE:
        ( A ) NAME/KEY: modified_base
        ( B ) LOCATION: 31
        ( D ) OTHER INFORMATION: /mod_base=i     (  x  i ) SEQUENCE DESCRIPTION: SEQ ID NO:4:

TACCTCGAGG TCGACGGTNA TGTGGTGYCC NTTYTTYAT  39

( 2 ) INFORMATION FOR SEQ ID NO:5:

(  i  ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     (  i  i  ) MOLECULE TYPE: other nucleic acid     (  i  i  i ) HYPOTHETICAL: NO     (  i  v ) ANTI-SENSE: NO     (  i  x ) FEATURE:
        ( A ) NAME/KEY: modified_base
        ( B ) LOCATION: 19
        ( D ) OTHER INFORMATION: /mod_base=i     (  i  x ) FEATURE:
        ( A ) NAME/KEY: modified_base
        ( B ) LOCATION: 25
        ( D ) OTHER INFORMATION: /mod_base=i     (  i  x ) FEATURE:
        ( A ) NAME/KEY: modified_base
        ( B ) LOCATION: 28
        ( D ) OTHER INFORMATION: /mod_base=i     (  i  x ) FEATURE:
        ( A ) NAME/KEY: modified_base
        ( B ) LOCATION: 31
        ( D ) OTHER INFORMATION: /mod_base=i     (  x  i ) SEQUENCE DESCRIPTION: SEQ ID NO:5:

AGAACTAGTG GTACCCARNG TRTANACNAR NGGRTT  36

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( i x ) FEATURE:
        ( A ) NAME/KEY: modified_base
        ( B ) LOCATION: 22
        ( D ) OTHER INFORMATION: /mod_base=i     ( i x ) FEATURE:
        ( A ) NAME/KEY: modified_base
        ( B ) LOCATION: 28
        ( D ) OTHER INFORMATION: /mod_base=i     ( x i ) SEQUENCE DESCRIPTION: SEQ ID NO:6:

AGAACTAGTG GTACCCSWRC ANACRTANCC DATCCA        36

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:7:

GATCCTGACT AACCGTTCTG GA        22

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:8:

TGCCTATTGA AATTAACCAT ACCA        24

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO

```
( i v ) ANTI-SENSE: NO ( x i ) SEQUENCE DESCRIPTION: SEQ ID NO:9:

TGCCTGGTTA TTCCTCGATG TTC                                                    23
```

POLYPEPTIDES HAVING A SEROTONIN RECEPTOR ACTIVITY, NUCLEIC ACIDS CODING FOR THESE POLYPEPTIDES AND USES

The present invention relates to new polypeptides and to the genetic material permitting their expression. More especially, it relates to new polypeptides having serotoninergic receptor activity.

Serotonin is a neuromodulator capable of inducing and modulating a wide variety of behavioural functions such as sleep, appetite, locomotion, sexual activity and vascular contraction. It is accepted that serotonin activity is mediated by its interaction with receptors, designated serotoninergic receptors or 5-HT (for 5-hydroxytryptamine) receptors. Molecular biology studies as well as pharmacological studies have revealed the existence of a large number of subtypes of 5-HT receptors. The 5-HT receptors which have been described to date belong either to the family of receptors associated with ion channels (5-HT3 receptors), or to the family of receptors which interact with G proteins and which possess seven transmembrane domains. Moreover, analysis of the amino acid sequences has shown that the 5-HT receptors which interact with G proteins may be subdivided into two distinct groups: 5HT1 receptors, comprising the mammalian subtypes 5HT1A, 5HT1B and 5HT1D, as well as three drosophila 5HT receptors; and 5HT2 receptors comprising the subtypes 5HT2 and 5HT1C.

These receptors are doubtless not the only 5HT receptors which exist, inasmuch as pharmacological studies have revealed other subtypes, such as 5HT4 receptors as well as some receptors related to the subtype 5HT1 ("5HT1-like" receptors). Furthermore, additional molecular biology studies have also revealed heterogeneities within the subtypes 5HT1B/1D.

Nowadays, contrary to the other subtypes, the 5HT2 receptors have not been widely studied. The 5HT2 receptors act via phospholipase C, and are responsible for numerous physiological activities of serotonin at the central and peripheral level. At the cardiovascular level, they are involved in the contraction of the blood vessels and in the morphological changes of the platelets; in the central nervous system, they act on the sensitization of the neurones to tactile stimuli and on the mediation of the hallucinogenic effects of diethylamidelysergic acid, and of the related phenylisopropylamines.

Numerous studies show that the 5HT2 receptors described up until now do not account for all the properties which are attributed to them. In particular, certain 5HT2-types effects of serotonin on the peripheral smooth muscles are classified as atypical effects, of which the effects are thought to be mediated by unknown receptors.

The present invention is the outcome of the demonstration of new polypeptides having serotoninergic receptor activity. While belonging to the family of receptors which interact with G proteins, these new polypeptides differ from the serotoninergic receptors already described (5HT1, 5HT2, 5HT3 and 5HT4) from both a structural standpoint and a pharmacological standpoint. More especially, the invention is the outcome of the isolation and characterization of these new polypeptides, designated 5HT2C, and also of the genetic material permitting their expression or identification. Pharmacological study of these receptors show that they could account for the atypical effects of serotonin which were previously observed.

A first subject of the invention hence lies in polypeptides comprising all or part of the peptide sequence SEQ ID No. 2 or of a derivative of the latter.

For the purposes of the present invention, the term derivative denotes any molecule obtained by modification, of a genetic and/or chemical nature, of the peptide sequence SEQ ID No. 2. Modification of a genetic and/or chemical nature may be understood to mean any mutation, substitution, deletion, addition and/or modification of one or more residues. Such derivatives may be generated for different purposes, such as, in particular, that of increasing the affinity of the peptide for its ligand(s), that of improving its levels of production, that of increasing its resistance to proteases, that of increasing and/or modifying its activity or that of endowing it with new pharmacokinetic and/or biological properties. Among derivatives resulting from an addition, chimeric polypeptides containing an additional heterologous portion attached at one end may, for example, be mentioned. The term derivative also comprises polypeptides homologous with the polypeptide SEQ ID No. 2, originating from other cell sources, and in particular from cells of human origin or of other organisms and possessing an activity of the same type. Such homologous polypeptides may be obtained by hybridization experiments, as described in the examples. In particular, Example 5 describes a derivative according to the invention (truncated form).

Preferably, the polypeptides of the invention are polypeptides possessing the capacity to bind serotonin. Still more preferably, they are polypeptides having serotoninergic receptor activity. Still according to a preferred embodiment, the polypeptides of the invention are capable of being recognized by antibodies which recognize the complete peptide sequence SEQ ID No. 2.

A particular embodiment of the invention is represented by the polypeptide 5HT2C comprising the whole peptide sequence SEQ ID No. 2. As shown in the examples, this polypeptide may be expressed in different cell types to form a functional serotoninergic receptor. This polypeptide comprises 479 amino acids and has a calculated molecular weight of 56,508 Daltons.

The polypeptides of the invention may be obtained by expression of a nucleotide sequence as described below in a cell host, by chemical synthesis on the basis of the sequence SEQ ID No. 2 using techniques known to a person skilled in the art, or by a combination of these techniques.

In what follows, the polypeptides of the invention as defined above are designated 5HT2C polypeptides.

The subject of the present invention is also any nucleotide sequence coding for a 5HT2C polypeptide. More preferably, such a sequence is chosen from:

(a) all or part of the nucleotide sequence SEQ ID No. 1 or of its complementary strand, (b) any sequence hybridizing with a sequence (a) and coding for a polypeptide as defined above, and (c) the sequences derived from the sequences (a) and (b) as a result of the degeneracy of the genetic code.

The different nucleotide sequences of the invention can be of artificial origin or otherwise. They can be genomic, cDNA or RNA sequences, hybrid sequences or synthetic or semi-synthetic sequences. These sequences may be obtained, for example, by screening DNA libraries (cDNA library, genomic DNA library) by means of probes devised on the basis of the sequence SEQ ID No. 1. Such libraries may be prepared from cells of different origins by standard techniques of molecular biology known to a person skilled in the art. The nucleotide sequences of the invention may also be prepared by chemical synthesis, in particular according to the phosphoramidite method, or alternatively by mixed methods including the chemical or enzymatic modification of sequences obtained by screening libraries.

The nucleotide sequences of the invention may be used for the production of 5HT2C polypeptides as defined above. In this case, the portion coding for the said polypeptide is generally placed under the control of signals permitting its expression in a cell host. The choice of these signals (promoters, terminators, and the like) can vary in accordance with the cell host used. To this end, the nucleotide sequences of the invention can form part of a vector, which can be an autonomously replicating or integrative vector. More especially, autonomously replicating vectors may be prepared using sequences which replicate autonomously in the chosen host. As regards integrative vectors, these may be prepared, for example, using sequences homologous with certain regions of the host's genome, permitting integration of the vector by homologous recombination. The cell hosts which are usable for the production of the 5HT2C polypeptides of the invention by the recombinant method are either eukaryotic or prokaryotic hosts. Among suitable eukaryotic hosts, animal cells, yeasts or fungi may be mentioned. In particular, as regards yeasts, yeasts of the genus Saccharomyces, Kluyveromyces, Pichia, Schwanniomyces or Hansenula may be mentioned. As regards animal cells, COS, CHO, C127 and NIH-3T3 cells, and the like, may be mentioned. Among fungi, *Aspergillus ssp.* or *Trichoderma ssp.* may be mentioned more especially. As prokaryotic hosts, it is preferable to use the following bacteria: *E. coli*, Bacillus or Streptomyces.

The nucleotide sequences of the present invention are also usable in the pharmaceutical field, either for the production of antisense sequences which may be used in the context of a gene therapy, or else for the production of probes permitting the detection, by hybridization experiments, of the expression of serotoninergic receptors in biological samples, and the demonstration of genetic abnormalities (polymorphism, mutations) or of aberrant expressions.

Inhibition of the expression of certain genes by antisense sequences has proved to be a promising strategy in controlling the activity of a gene. The antisense sequences are DNA sequences coding for complementary RNAs and, therefore, capable of hybridizing specifically with a given mRNA, inhibiting its translation into protein. A subject of the invention is thus the antisense sequences capable of at least partially inhibiting the production of 5HT2C polypeptides as defined above. Such sequences can consist of all or part of the nucleotide sequences defined above. They are generally sequences or fragments of sequences complementary to sequences coding for peptides of the invention. Such sequences may be obtained from the sequence SEQ ID No. 1, by fragmentation, and the like, or by chemical synthesis.

As stated above, the invention also makes it possible to produce nucleotide probes, synthetic or otherwise, capable of hybridizing-with the nucleotide sequences defined above which code for 5HT2C polypeptides of the invention, or with the corresponding mRNAs. Such probes may be used in vitro as a diagnostic tool for detecting the expression of a 5HT2C serotoninergic receptor, or alternatively for demonstrating genetic abnormalities (incorrect splicing, polymorphism, point mutations, and the like). In view of the numerous activities of serotonin, the probes of the invention may thus enable neurological, cardiovascular or psychiatric disorders to be identified as being associated with 5HT2C receptors. These probes may also be used for demonstrating and isolating homologous nucleic acid sequences coding for 5HT2C polypeptides as defined above, from other cell sources and preferably from cells of human origin, as illustrated in the examples. The probes of the invention generally contain at least 10 bases, and they can contain as much as the whole of the sequence SEQ ID No. 1 or of its complementary strand. Preferably, these probes are labelled prior to their use. For this purpose, different techniques known to a person skilled in the art may be employed (radioactive or enzymatic labelling, and the like). The hybridization conditions under which these probes may be used are mentioned in the general cloning techniques below, as well as in the examples.

Another subject of the invention relates to recombinant cells capable of expressing at their surface a 5HT2C polypeptide as defined above. These cells may be obtained by introducing a nucleotide sequence as defined above, coding for a polypeptide of the invention, and then culturing the said cells under conditions for expression of the said sequence.

The recombinant cells according to the invention can be either eukaryotic or prokaryotic cells. Among suitable eukaryotic cells, animal cells, yeasts or fungi may be mentioned. In particular, as regards yeasts, yeasts of the genus Saccharomyces, Kluyveromyces, Pichia, Schwanniomyces, or Hansenula may be mentioned. As regards animal cells, COS, CHO, C127 and NIH-3T3 cells, and the like, may be mentioned. Among fungi, *Aspergillus ssp.* or *Trichoderma ssp.* may be mentioned more especially. As prokaryotic cells, it is preferable to use the following bacteria: *E. coli*, Bacillus or Streptomyces. The cells thereby obtained may be used to measure the ability of different molecules to behave as a ligand or as a modulator of the activity of the polypeptides of the invention. More especially, they may thus be used in a method for demonstrating and isolating ligands or modulator of the activity of the polypeptides of the invention, and more preferably serotonin agonists and antagonists.

Another subject of the invention hence relates to a method for demonstrating and/or isolating ligands of the 5HT2C polypeptides of the invention, according to which the following steps are carried out:

a molecule or a mixture containing different molecules, which are possibly unidentified, is brought into contact with a recombinant cell as described above, expressing at its surface a polypeptide of the invention, under conditions permitting interaction between the said polypeptide of the invention and the said molecule should the latter possess an affinity for the said-polypeptide, and the molecules bound to the said polypeptide of the invention are detected and/or isolated.

In a particular embodiment, this method of the invention is suitable for demonstrating and/or isolating serotonin agonists and antagonists for the 5HT2C polypeptides.

Another subject of the invention relates to a method for demonstrating and/or isolating modulators of the 5HT2C polypeptides of the invention, according to which the following steps are carried out:

a molecule or a mixture containing different molecules, which are possibly unidentified, is brought into contact with a recombinant cell as described above, expressing at its surface a polypeptide of the invention, in the presence of 5HT, under conditions permitting interaction between the said polypeptide of the invention and 5HT, and the molecules capable of modulating the activity of 5HT with respect to the said polypeptide of the invention are detected and/or isolated.

Another subject of the invention relates to the use of a ligand or modulator identified and/or obtained according to the method described above, as a medicinal product. Such ligands or modulators can, in effect, enable certain neurological, cardiovascular or psychiatric disorders associated with 5HT2C receptors to be treated.

The invention also relates to any medicinal product comprising as active principle at least one molecule which acts on a 5HT2C polypeptide of the invention. Preferably, the molecule is a ligand or a modulator identified and/or isolated according to the method described above.

Other advantages of the present invention will become apparent on reading the examples which follow, which are to be considered as illustrative and nonlimiting.

LEGEND TO THE FIGURES

Table 1 Pharmacological profile of the whole (N) or truncated (T) 5HT2C receptor. The results correspond to competition experiments for the binding of [$^{125}$I]DOI to the membranes of Cos-7 cells expressing the 5HT2C receptor. The values, expressed as pKD (-log mol/1) are the result of at least three separate experiments, carried out in triplicate.

GENERAL CLONING TECHNIQUES

The methods traditionally used in molecular biology,- such as preparative extractions of plasmid DNA, centrifugation of plasmid DNA in a caesium chloride gradient, agarose or acrylamide gel electrophoresis, purification of DNA fragments by electroelution, protein extractions with phenol or phenol/chloroform, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York 1987].

The restriction enzymes, AMV reverse transcriptase, DNA polymerase I, T4 polynucleotide kinase, T4 DNA ligase, and T3 or T7 RNA polymerases were supplied by New England Biolabs (Biolabs), Bethesda Research Laboratories (BRL), Boehringer-Mannheim or Stratagene and are used according to the suppliers' recommendations.

For ligation, the DNA fragments are separated according to size by agarose or acrylamide gel electrophoresis, extracted with phenol or with a phenol/chloroform mixture, precipitated with ethanol and then incubated in the presence of phage T4 DNA ligase according to the supplier's recommendations.

The filling-in of 5' protruding ends is performed with the Klenow fragment of *E. coli* DNA polymerase I according to the supplier's specifications. The destruction of 3' protruding ends is performed in the presence of phage T4 DNA polymerase used according to the manufacturer's recommendations. The destruction of 5' protruding ends is performed by a controlled treatment with S1 nuclease.

Mutagenesis directed In vitro by synthetic oligodeoxynucleotides is performed according to the method developed by Taylor et al. [Nucleic Acids Res. 13 (1985) 8749–8764].

The enzymatic amplification of DNA fragments by the so-called PCR [Polymerase-catalyzed Chain Reaction, Saiki R. K. et al., Science 230 (1985) 1350–1354; Mullis K. B. and Faloona F. A., Meth. Enzym. 155 (1987) 335–350] technique is performed using a "DNA thermal cycler" (Perkin Elmer Cetus) according to the manufacturer's specifications.

Verification of the nucleotide sequences is performed by the method developed by Sanger et al. [Proc. Natl. Acad. Sci. USA, 74 (1977) 5463–54673].

For the hybridization experiments, the normal conditions of stringency are generally as follows: hybridization: 5× SCC in the presence of 5× Denhart's at 65° C.; washing: 0.5× SSC at 65° C.

1. Isolation of the 5HT2C Receptor

Sequence comparisons between the different known serotoninergic receptors bring out some degree of conservation. With the aim of demonstrating and isolating a new receptor, three degenerate oligonucleotides corresponding to the VI and VII transmembrane regions were prepared and then used in a series of PCR reactions on a mouse genomic DNA preparation. The sequence of the degenerate oligonucleotides is the following:

Oligonucleotide (i) (SEQ ID No. 4 ) TACCTCGAGGTCGACGGTIATGTGGTG(C,T)CCITT (C,T)TT(C,T)AT Oligonucleotide (ii) (SEQ ID No. 5 ) AGAACTAGTGGTACCCA(G,A)IGT(G,A)TAIACIA(G,A)IGG(G,A)TT Oligonucleotide (iii) (SEQ ID No. 6 ) AGAACTAGTGGTACCC(G,C) (A,T) (G,A) (G,A)TAICC (G,A,T)ATCCA A multiple cloning site was added to the 5' end of the oligonucleotides to allow subsequent subcloning of the amplified fragment. The PCR reactions were performed in the following manner: 1 µg of mouse genomic DNA was denatured for 1 minute at, 94° C., maintained for 2 minutes at 55° C. and then subjected to 20 amplification cycles at 72° C. in the presence of 10 Taq polymerase units (Cetus), 3 mM MgCl$_2$ and 1 µg of each of the oligonucleotides (i) and (ii). 1/10 th of the product of this reaction was then subjected to 20 additional amplification cycles under the same conditions, in the presence of 1 µg of each of the oligonucleotides (i) and (iii). The products thus obtained were then digested with the SpeI and XhoI enzymes, inserted into the corresponding sites of the plasmid Bluescript (Strategene), and sequenced. One of the fragments thus obtained, having some homology with the 5HT2 serotoninergic receptors, was synthesized in vitro and labelled at its 5' end by polynucleotide kinase, and then used as a probe to screen a mouse brain cDNA library. A positive clone was selected. This clone was designated NP75. The insert carried by the NP75 clone was sequenced on the 2 strands using the dideoxynucleotide technique with the aid of synthetic oligonucleotides. Analysis of the sequence obtained reveals the presence of an open reading frame coding for a protein of 479 amino acids (SEQ ID No. 1 and 2). Moreover, analysis of hydrophobicity shows that this protein carries seven hydrophobic domains, a characteristic encountered in members of the family of receptors coupled to G proteins. The N-terminal end contains, moreover, 1 potential site for N-glycosylation, and the presumed cytoplasmic domain contains the consensus sites for phosphorylation by the C and A protein kinases. In addition the presence of 19 serine and threonine residues in the 121 C-terminal amino acids seems to indicate that this region is involved in the desensitization of the receptor by kinases.

2. Sequence Homology Study

The sequence of the 5HT2C receptor isolated above was compared with the sequences of the following receptors coupled to G proteins: 5HT1A, 5HT1B, 5HT1C, and 5HT2. These experiments revealed homology in the I to VII transmembrane domains with the 5HT1C and 5HT2 receptors greater than the homology encountered with the 5HT1A and 5HT1B receptors. These results suggest, that the receptors of the invention belong to the 5HT2 subtype. This is in fact in agreement with the presence of 2 introns in the gene coding for the 5HT2C receptor (not shown in the sequence).

3. Expression of the 5HT2C Receptor in Cos-7 Cells and Pharmacological Characterization The cDNA fragment isolated in Example 1 was inserted into an eukaryotic expression vector, which was used to transfect Cos-7 cells. The membranes of the transfected cells obtained were then prepared and tested for their capacity to bind certain labelled serotoninergic ligands.

The cDNA encoding the 5HT2C receptor was isolated in the form of a 1372 pb XbaI-EcoRI fragment and then inserted at the corresponding sites of the vector p513. The vector p513 is derived from the vector pSG5 [Green et al., Nucl. Acids Res. 16 (1988) 369] by addition of a multiple cloning site. The recombinant vector thus obtained, designated p513NP75, was then used (10 μg per 10 cm dish) to transfect the Cos-7 cells in the presence of calcium phosphate.

48 Hours after transfection, the recombinant cells are harvested and the membranes are prepared according to the technique described by Amlaiky and Caron [J. Biol. Chem. 260 (1985) 1983].

Saturation binding and competition experiments were then carried out on these membranes in the presence of [$^{125}$I]DOI (2200 Ci/mmol; New England Nuclear) and various test compounds.

The [$^{125}$I]DOI (dimethoxyphenyl isopropylamine) was first used alone, in order to detect the expression of the gene encoding the receptors of the invention in the membranes of the recombinant cells. For this purpose, 100 μl of membrane suspension (50 μl) of proteins) were incubated for 30 minutes at 30° C. in the presence of the radioactive ligand (50 μl) and 50 μl of 50 mM Tris-HCl buffer (pH 7.4), 150 mM NaCl, 10 mm MgCl$_2$, final volume: 200 μl. The reaction is then stopped by addition of an isoosmotic ice-cold solution, then by filtration on Whatman GF/B filters, followed by 4 rinses in 5 ml of the above ice-cold buffer. The filters are then dried and the radioactivity is measured by counting (γ counter). Non-specific binding, determined in the presence of 10 μM of cold DOI, represented about 30% of the total binding.

Figure 1:
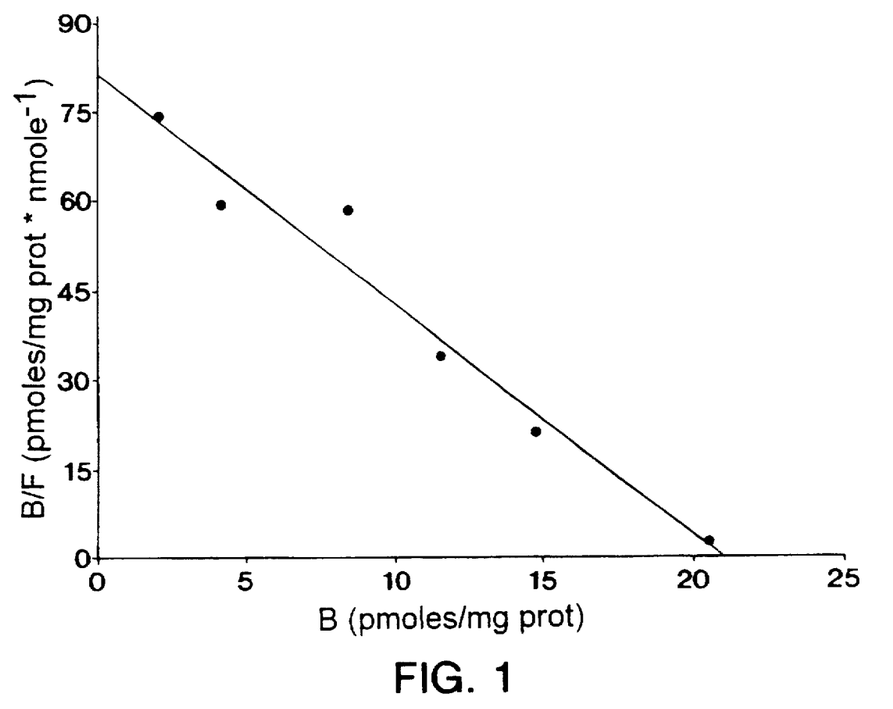
FIG. 1 Scatchard curve of the results of experiments for the binding, at saturation, of [$^{125}$I]DOI to the membranes of Cos-7 cells expressing the 5HT2C receptor.

The results obtained show that DOI binds specifically to the membranes of the transfected cells, and not to the membranes of the control cells (transfected with plasmid pSG5). These cells therefore indeed express a functional serotonin receptor. Furthermore, the affinity of DOI for the transfected cells is high and the binding is saturable (FIG. 1). The apparent KD is 25.8±0.54 nM, and the apparent Bmax varies between 14.8 and 21.0 pmol/mg of protein, depending on the transformation efficiency.

To determine the pharmacological profile of this receptor, the [$^{125}$I]DOI bound to the membranes was displaced in the presence of different serotoninergic drugs (Table 1). For this purpose, the cellular membranes are incubated under the conditions described above, with, in place of the 50 μl of buffer, increasing concentrations of the compounds to be tested. These different drugs show the following order of efficacy of displacement: ritanserin>N-acetyl 5-HT>methysergide>setoperone=cyproheptadine>spiperone>ketanserin>tryptamine>5-HT>8-OH-DPAT (Table 1). The low affinity (relative) of this receptor for serotonin confirms that it belongs to the 5HT2 subtype. Furthermore, the absence of competition by the compounds ICS 205–930, MDL 72222 and quipazine, which are specific for the 5HT3 receptors, excludes the possibility that the receptors of the invention belong to this subtype.

4. Search for Homologous Sequences in Other Tissues

The nucleotide sequence SEQ ID No. 1 was then used to demonstrate homologous sequences on other tissues by PCR.

The tissues used to search for homologous sequences are the following ones of murine origin: intestine, heart, brain, kidney, spleen and liver.

The following probes were used:

Probe (iv): 5'-GATCCTGACTAACCGTTCTGGA-3' (SEQ ID No. 7)

Probe (v): 5'-TGCCTATTGAAATTAACCATACCA-3 (SEQ ID No. 8)

Probe (iv) corresponds to position 85 on SEQ ID No. 1 and probe (v) to position 547 (complementary strand).

Total RNAs were prepared from the tissues indicated above according to the technique described by Cathala et al. (DNA 2(4) (1983). 10 μg of these RNAs were subjected to reverse transcription in the presence of 13 units of AMV reverse transcriptase, 5 units of Taq polymerase and 1 μg of probes (iv) and (v), for 15 minutes at 50° C., and then amplified (20, 25 and 30 cycles) (Maroteaux et al., Proc. Natl. Acad. Sci. USA 89 (1992) 3020). The primers corresponding to the mRNA of the ribosomal elongation factor EF1A were used as internal standard, under the same conditions as probes (iv) and (v).

The products thus obtained were then transferred onto nitrocellulose filters and hybridized under the following conditions: the probe used for the hybridization had the following sequence:

Probe (vi): 5'-TGCCTGGTTATTCCTCGATGTTC-3' (SEQ ID No. 9)

corresponding to position 398 on the sequence SEQ ID No. 1.

The hybridization was carried out under high stringency conditions: 50° C., in a 20 mM sodium phosphate buffer (pH 6.5) containing 5× SSC, 1× Denhardt's 0.1% SDS and 100 μg/ml of tRNA. The washes were performed at 50° C. in 1× SSC, 0.1% SDS buffer.

Figure 2A:
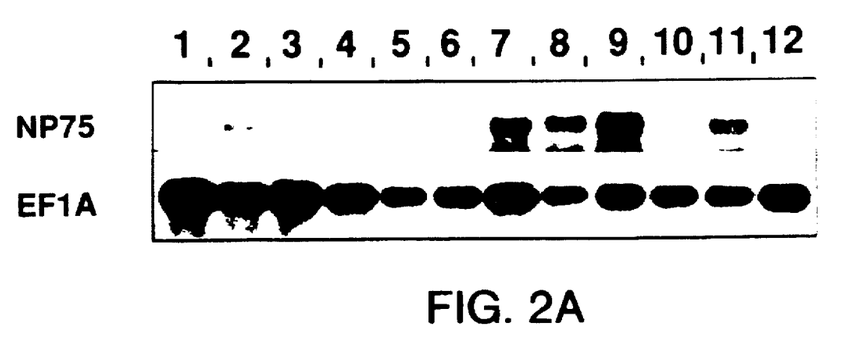
FIG. 2 Demonstration of homologous sequences by PCR on total RNAs (10 µg) of different mouse tissues: line 1: RNA from the LMTK cell line, line 2: RNA from 10-day old embryos, line 3: RNA from testicles, line 4: RNA from the 3T6 cell line, line 5: RNA from the MBK cell line, line 6: RNA from the liver, line 7: RNA from the brain, line 8: RNA from the heart, line 9: RNA from the intestine, line 10: RNA from the spleen, line 11: RNA from the kidney, line 12: total RNA from the brain.
Figure 2B:
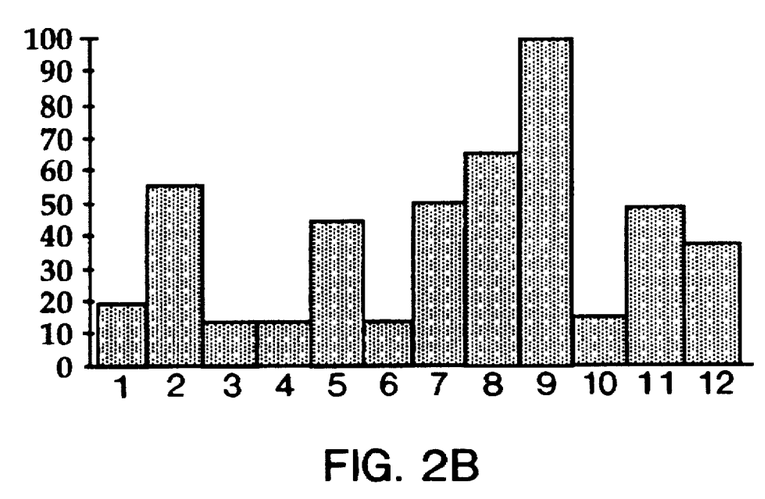

This study enabled homologous specific DNA fragments to be demonstrated in the intestine, the heart, the kidneys and the brain (FIG. 2).

It is understood that the same experiments can be repeated using other tissues and especially tissues of human origin, other probes, and other techniques (in situ hybridization, Northern blotting and the like). Moreover, the homologous sequences demonstrated during these experiments can obviously then be isolated and/or amplified by conventional molecular biology techniques.

5. Isolation and Characterization of a Truncated Receptor SEQ ID No. $2_{(1-177)}$-SEQ ID No. 3

During the cloning of the cDNA encoding the 5-HT2C receptor (Example 1), numerous forms of truncated mRNA were identified. One of them, after characterization, turned out to encode a receptor having only the first three transmembrane domains [residues 1 to 177 SEQ ID No. 2, to which the following 14 C-terminal amino acids can be added: Ala Ser Pro Ser Gln Ser Leu Leu Lys Glu Ser Arg Leu Met (SEQ ID No. 3)] Analysis of the organization of the genomic DNA shows that this RNA is obtained from the use of an alternative donor for splicing at the end of exon 2 resulting in the removal of bases 550–568 from the nucleic sequence SEQ ID No. 1. This causes a change of phase and introduces a stop codon into the RNA, producing a truncated protein after the third transmembrane domain. This alternative form of mRNA, first isolated from brain RNA, is differentially expressed depending on the tissues. The relative level of expression of the truncated RNA compared with the complete RNA is maximum in mouse heart, where it represents more than 50%, whereas it is only 15% in the intestine.

Unexpectedly, analysis of the pharmacological profile of this truncated protein by transient expression in COS cells according to the method described in Example 3 shows that it binds serotonin with an affinity very close to that observed for the complete receptor (Table 1). Furthermore, its affinity for agonists remains, although slightly reduced, whereas the binding for antagonists is completely abolished, as well as the translation of the intracellular signal. The physiological role of this form of the receptor remains unknown, but it seems likely that it serves to protect certain sensitive targets, such as the vascular endothelium, from harmful stimulations by locally "diluting" the effect of the ligand, in this case serotonin.

Finally, more precise analysis, by in situ hybridization, of the sites of expression of the 5-HT2C receptor in mouse heart situates them in the endocardial and vascular endothelium. This expression is also detected in the inner layer (endothelium) of cardiac anlages in mouse early embryos (8.5 days). Knowing that serotonin is involved in the phenomena of development of the cardiovascular system in chicken embryo (Heuther et al., Biog Amine 8 (1992) 421), it is possible that the 5-HT2C receptor participates in these phenomena. Likewise, recent observations implicate serotonin in the pathophysiology of coronary diseases: human coronary atherosclerosis is associated with an increased sensitivity to serotonin of the contraction of the coronary arteries. This phenomenon can be reduced by ketanserin (Golino et al., New Engl. J. Med. 324 (1991) 641) and results from lesions of the vascular endothelium where serotonin is released by the platelets. It is thus likely that the truncated 5-HT2C receptor-expressed in the vascular endothelium participates in the regulation of the effect of serotonin on the cardiovascular system both during its differentiation and its pathological deregulation.

Consequently, the development of compounds specific for the whole or truncated 5-HT2C receptor is of therapeutic value in certain human cardiac pathologies.

TABLE 1

| Compounds | Binding to the COS N cells | COS T | 5-HT2 | 5-HT1C |
| --- | --- | --- | --- | --- |
| Agonists | | | | |
| N-Acetyl-5-HT | 8.15 | 6.70 | 5.5 | 6.1 |
| 5-HT | 5.90 | 5.93 | 5.5 | 7.5 |
| 2-Me-5-HT | 5.18 | <4.0 | 5.2 | 5.8 |
| Tryptamine | 6.70 | 4.84 | 6.0 | 7.2 |
| 1-ME-5-HT | 5.60 | 4.22 | 6.3 | 8.4 |
| NNdiMe-5-MeOT | 5.13 | 4.34 | 6.2 | 7.0 |
| 8-OH-DPAT | 5.19 | <4.0 | 5.0 | 5.2 |
| Quipazine | 5.18 | 4.85 | 6.2 | 6.7 |
| Histamine | <4.0 | <4.0 | <4.0 | <4.0 |
| Antagonists | | | | |
| Ritanserin | 8.44 | <4.0 | 9.3 | 8.6 |
| Methysergide | 7.90 | <4.0 | 8.6 | 8.6 |
| Setoperone | 7.61 | <4.0 | 8.6 | 7.3 |
| Cyproheptadine | 7.65 | <4.0 | 8.5 | 7.9 |
| Spiperone | 7.30 | <4.0 | 8.8 | 5.9 |
| Ketanserin | 6.69 | <4.0 | 8.9 | 7.0 |
| ICS 205-930 | 5.30 | <4.0 | 5.3 | 4.6 |
| MDL 72222 | 4.62 | <4.0 | 6.7 | <5.0 |
| Chlorpromazine | <4.0 | <4.0 | <4.0 | <4.0 |

I claim:

1. An isolated polypeptide comprising a sequence selected from the group consisting of:
   (a) SEQ ID No. 2
   (b) SEQ ID No. $2_{(1-177)}$-SEQ ID No. 3. and
   (c) fragments of (a) or (b), wherein said polypeptide has serotonin binding activity.

2. An isolated nucleic acid having a sequence coding for a polypeptide according to claim 1, or the complementary strand of said nucleic acid.

3. A nucleic acid according to claim 2, comprising nucleotides 19–1455 of SEQ ID No. 1 or its complementary strand.

4. A nucleic acid according to claim 2, selected from the group consisting of genomic sequences, cDNA sequences, RNA sequences, synthetic sequences and semi-synthetic sequences.

5. A nucleic acid according to claim 2, wherein the coding sequence is placed under the control of signals permitting expression of the polypeptide in a host cell.

6. A recombinant cell comprising a nucleic acid according to claim 2.

7. A recombinant cell according to claim 6, characterized in that it is a eukaryotic cell.

8. A recombinant cell according to claim 6, characterized in that it is a prokaryotic cell.

9. A vector comprising the nucleic acid of claim 2.

10. A method for demonstrating and/or isolating ligands of the polypeptides as defined in claim 1, comprising:
   contacting a molecule or a mixture containing different molecules with a recombinant cell expressing at its surface a polypeptide as defined in claim 1, under conditions permitting interaction between the said polypeptide and the said molecule, and
   detecting and/or isolating molecules bound to the said polypeptide.

11. A method for demonstrating and/or isolating modulators of the polypeptides as defined in claim 1, comprising:
   contacting in the presence of 5HT a molecule or a mixture containing different molecules with a recombinant cell expressing at its surface a polypeptide as defined in claim 1 under conditions permitting interaction between the said polypeptide and 5HT, and
   detecting and/or isolating molecules capable of modulating the activity of 5HT with respect to the said polypeptide.

* * * * *